United States Patent [19]

Morrow et al.

[11] Patent Number: 4,537,689
[45] Date of Patent: Aug. 27, 1985

[54] ORAL LUBRICANT FOR ATHLETIC MOUTH PROTECTOR

[75] Inventors: Robert M. Morrow; William A. Kuebker, both of San Antonio; James W. McGinity, Austin, all of Tex.

[73] Assignee: The Board of Regents, University of Texas System, Austin, Tex.

[21] Appl. No.: 563,239

[22] Filed: Dec. 19, 1983

[51] Int. Cl.$^3$ .......................... C10M 5/00; C10M 1/06
[52] U.S. Cl. ....................................... 252/11; 252/20; 252/49.5
[58] Field of Search ........................ 252/11, 20, 49.5; 128/136; 424/49

[56] References Cited

U.S. PATENT DOCUMENTS

| | | | |
|---|---|---|---|
| 2,773,801 | 12/1956 | Fox | 424/49 |
| 3,016,052 | 1/1962 | Zubren | 128/136 |
| 3,431,208 | 3/1969 | Bailey | 424/49 |
| 3,840,657 | 10/1974 | NorFleet | 424/49 |
| 3,842,167 | 10/1974 | Block | 424/49 |
| 4,405,599 | 9/1983 | Smigel | 424/49 |
| 4,459,283 | 7/1984 | Harvey | 424/49 |
| 4,465,661 | 8/1984 | Schmolka | 424/49 |

OTHER PUBLICATIONS

Shannon, I. L. et al., "A Saliva Substitute for Use by Xerostomic Patients Undergoing Radiotherapy to the Head and Neck", vol. 44, No. 5, Oral Surgery, pp. 656–661, Nov. 1977.
Dennis, C. G., D.D.Sc. et al., "Mouthguards in Australian Sport", vol. 17, Australian Dental Journal, pp. 228–235, Jun. 1972.
Turner, C. H., "Mouth Protectors", vol. 143, No. 82, British Dental Journal, pp. 82–86, Aug. 1977.
Nachman, Benjamin M. et al., "Football Players' Opinions of Mouthguards", vol. 70, The Journal of the American Dental Association, pp. 62–69, Jan. 1965.
Bureau of Dental Health Education and Bureau of Economic Research and Statistics, "Evaluation of Mouth Protectors Used by High School Football Players", vol. 68, The Journal of the American Dental Association, pp. 430–442, Mar. 1964.
Jar Label, "Xero-Lube" Saliva Substitute, NDC 0274-2365-06, Scherer Laboratories, Inc., (no date).
Braham, Raymond L. et al., "Management of Dental Trauma in Children and Adolescents", vol. 17, No. 11, The Journal of Trauma, pp. 857–865, Nov. 1977.
de Wet, F. A., "The Prevention of Orofacial Sports Injuries in the Adolescent", vol. 31, No. 4, Int. Dental Journal, pp. 313–319, 1982.
de Wet, F. A., "Mouthguards for Rugby Players at Primary School Level", vol. 36, Journal of the Dental Association of South Africa, pp. 249–253, 1981.

*Primary Examiner*—John F. Niebling
*Attorney, Agent, or Firm*—Arnold, White & Durkee

[57] ABSTRACT

An oral lubricant effective in reducing the discomfort associated with the wearing of a mouth protector during periods of activity consisting essentially of a thickening agent, a preservative, a flavoring agent, a sweetener, an emulsifier, if needed, and a liquid diluent.

14 Claims, No Drawings

ORAL LUBRICANT FOR ATHLETIC MOUTH PROTECTOR

BACKGROUND OF THE INVENTION

The present invention concerns oral lubricants for mouth protectors; more specifically, it relates to a lubricating composition effective to reduce the discomfort of wearing athletic mouth protectors.

In many contact sports, athletes wear plastic mouth protectors to guard against injury to the teeth, gums and other structures of the oral cavity. The protection provided by the protectors is quite effective. Despite this useful protection, the mouth protector can be uncomfortable to wear.

During the physical exertion and excitement of athletic competition, the athlete's oral cavity becomes quite dry. As a result, the plastic mouth protector adheres to the teeth and dry mucous membranes, a condition known as xerostomia, causing the athlete discomfort. In addition, athletes may experience difficulty in breathing and speech disturbances. The plastic taste of the mouth protector further adds to these discomforts and inconveniences. Consequently, some athletes prefer the risk of not wearing a mouth protector to the discomfort of its use. The probability that the athlete will choose not to wear a mouth protector is particularly high during practice, but it is also likely during games when referees are not actively enforcing the rules which require the wearing of mouth protectors.

Because of the risk of serious injury and the difficulty of enforcing the rules which require the use of mouth protectors, there is a substantial need for a means to eliminate the problems associated with the wearing of a mouth protector. Applicants are not aware of any prior oral lubricant effective to eliminate the problems caused by the wearing of mouth protectors.

The use of saliva substitutes is well known. Such artificial saliva compositions are formulated specifically for use by patients such as those who are undergoing radiotherapy to the head or neck because the radiation therapy severely depresses salivary gland function. See Shannon, I. L., McCrary and E. N. Starke, "A Saliva Substitute for Use By Xerostomic Patients Undergoing Radiotherapy to the Head and Neck," *Oral Surgery*, vol. 44, no. 5, (Nov. 1977), pp. 656–661. However, the formulations of these saliva substitutes are made up to approximate the composition of normal human saliva as closely as possible. The simulation of the composition of normal human saliva is necessitated by the fact that such patients experience a variety of problems such as increased dental caries, changes to intraoral soft tissues such as cracking and bleeding of the mucosa, decreased hardness of the enamel and painful swallowing, all associated with the impaired function of the salivary glands.

As can be seen, such saliva substitutes are not formulated primarily to lubricate, but rather for therapeutic purposes. Consequently, they do not contain the appropriate ingredients and the appropriate concentrations of the appropriate ingredients to allow their use as lubricants for athletic mouth protectors. Testing conducted by Applicants indicates that saliva substitutes are totally inadequate as a lubricant for mouth protectors during periods of physical exertion and that saliva substitutes do not eliminate the disagreeable taste of the mouth protector.

Further, many saliva substitutes contain additional ingredients which are inappropriate or unnecessary for use in a lubricant for athletic mouth protectors. In particular, the relatively high electrolyte content of saliva substitutes, a result of the formulation of the composition so as to simulate normal human saliva, makes them unsuitable for use in periods of strenuous activity.

It is also known in the art to formulate a mouth protector of a plastic or vinyl resin impregnated with a flavoring such as mint flavoring. Wearers of such mouth protectors do not experience significant improvement in the frequency of xerostomic conditions. Further, the amount of flavoring released by the mouthguard continually decreases until a point is reached at which the amount of flavoring released is insufficient to overcome the unpleasant taste of the mouthguard.

SUMMARY OF THE INVENTION

The present invention relates to reducing the discomfort of wearing an athletic mouth protector, wherein a lubricating composition is applied to the mouth protector prior to insertion. The composition consists of a lubricating agent, a thickening agent, a preservative, a pharmaceutically suitable flavoring agent, and a pharmaceutically suitable sweetener, admixed together with a liquid diluent. The composition may additionally contain an emulsifier.

Such a composition is useful to reduce the discomfort associated with the wearing of a mouth protector by an athlete during periods of exertion. Increased wearing of mouth protectors helps reduce the number of injuries to the structures of the oral cavity suffered by athletes participating in contact sports.

DETAILED DESCRIPTION OF THE INVENTION

The present invention relates to reducing the discomfort of wearing mouth protectors through the use of lubricating compositions. By applying the lubricating composition to the mouth protector prior to insertion of the mouth protector into the oral cavity, the user will help prevent the drying of the oral cavity which causes the mouth protector to adhere to the teeth and the dry mucous membranes.

The prevention of such adherence is accomplished by the inclusion of a lubricating agent such as glycerin, a syrupy, viscous liquid in the lubricating composition. In addition to the lubricating agent, the composition contains (1) a thickening agent, (2) a preservative, (3) a flavoring agent, (4) a sweetener, (5) an emulsifier, if needed, and (6) a diluent.

Applicants have utilized glycerin as a lubricating agent. However, it is expected that high molecular weight compositions such as propylene glycol or polyethylene glycol could be used in place of or in conjunction with glycerin.

Thickening agents are utilized to increase the viscosity of the composition. Depending upon the particular thickening agent utilized, the thickening agent can also help to maintain the stability of the composition and to enhance its emulsifying qualities. Generally, any hydrophilic polymer which has a viscosity higher than that of water and also has some lubricating properties will suffice. A thickening agent found to be particularly effective by Applicants is methylcellulose. In particular, sodium carboxymethyl cellulose may be utilized because of its ability to solubilize readily. Applicants have used medium viscosity sodium carboxymethyl cellulose, purchased from City Chemical, New York, N.Y., to advantage. Hydrophilic polymers such as ethyl cellulose and other alkyl derivatives of these cellulose may also be used, as well as naturally occurring gums (acacia, any one of the alginates, tragacanth, agar, or guar gum), or a synthetic hydrophilic polymer, such as polyvinylpyrrolidone (i.e., PVP K-30 ® or PVP K-90 ® (GAF Corp.)) or one of the vinyl polymers (i.e., Carbopol 930 ® or Carbopol 934 ® (B. F. Goodrich Chemical Co.)).

Other thickening agents which may be utilized to advantage include the microfine clays. In particular, Veegum F ®, a microfine grade of colloidal magnesium aluminum silicate (R. T. Vanderbilt Company, Norwich, CT) has been utilized, but there are other grades of this clay available which may also be used. Other agents which may be effectively used include bentonite, kaolin and kilselguhr.

Preservatives are used to help prevent the growth of microorganisms in the lubricating composition or the degradation of the composition by microorganisms. Two preservatives which have been used to advantage, both by themselves or in combination, are methyl paraben and propyl paraben.

Flavoring agents and sweeteners improve the taste of the lubricating composition. The number of flavor extracts and oils which may be used is limited only by the preferences of the athletes who use the lubricating composition. Applicants have used peppermint oil, citrus oil and spearmint oil. Any natural or artifical sweetener may be utilized; Applicants have found sodium saccharin to be a suitable sweetener.

An emulsifier helps to hold the flavoring oil, which is immiscible in water-based liquids, in suspension. Applicants prefer polysorbate 80 (polyoxyethylene (20) sorbitan monooleate), available commercially from a variety of suppliers as an emulsifier. However, when colloidal thickening agents such as Veegum F ® are used, it has been found generally unnecessary to use the emulsifier, because the flavoring oil is held in suspension by virtue of being absorbed onto the surface of the clay particles.

The diluent reduces the concentrations of the active components to an effective level. Applicant has found water to be particularly effective as a diluent. For ease in handling, the composition may be formulated in a solution without the diluent. The user may then add the diluent and mix the solution into it in the proper concentrations.

The lubricating composition of the present invention is applied to the mouth protector before the mouth protector is inserted into the mouth. The composition may be poured or sprayed onto the mouth protector, or the mouth protector may be dipped into a container of the composition.

Applicants prefer the following formulations of the present invention. These formulations are presented by way of example only and are in no way to be construed as a limitation of the scope of the present invention.

EXAMPLE 1

| Glycerin | 100 ml |
| --- | --- |
| Sodium Carboxymethylcellulose | 0.45% (wt/vol) |
| Sodium Saccharin | 0.1 g |
| Spearmint Oil | 0.375 ml |
| Methyl Paraben | 0.75 g |
| Propyl Paraben | 0.25 g |
| Water q.s. | 500 ml |

EXAMPLE 2

| Glycerin | 100 ml |
| --- | --- |
| Veegum F ® | 2.4% (wt/vol) |
| Sodium saccharin | 0.1 g |
| Peppermint Oil | 0.75 ml |
| Methyl Paraben | 0.5 g |
| Propyl Paraben | 0.1 g |
| Water q.s. | 500 ml |

EXAMPLE 3

| Glycerin | 100 ml |
| --- | --- |
| Veegum F ® | 2.4% (wt/vol) |
| Sodium Saccharin | 0.1 g |
| Peppermint Oil | 0.375 ml |
| Methyl Paraben | 0.5 g |
| Propyl Paraben | 0.1 g |
| Water q.s. | 500 ml |

EXAMPLE 4

| Glycerin | 100 ml |
| --- | --- |
| Sodium Carboxymethylcellulose | 0.45% (wt/vol) |
| Sodium Saccharin | 0.1 g |
| Spearmint Oil | 0.75 ml |
| Methyl Paraben | 0.75 g |
| Propyl Paraben | 0.25 g |
| Water q.s. | 500 ml |

EXAMPLE 5

| Glycerin | 20 ml |
| --- | --- |
| Methocel (Dow Chemical Co.) 8% (wt/vol) | 30 ml |
| Peppermint Oil | 1 ml |
| Polysorbate 80 | 2 ml |
| Sodium Saccharin | 20 mg |
| Methyl Paraben | 200 mg |
| Water | 100 ml |

EXAMPLE 6

| Glycerin | 20 ml |
| --- | --- |
| Veegum F ® 8% (wt/vol) | 30 ml |
| Sodium Saccharin | 20 mg |
| Peppermint Oil | 1 ml |
| Polysorbate 80 | 2 ml |
| Methyl Paraben | 200 mg |
| Water | 100 ml |

EXAMPLE 7

| Glycerin | 100 ml |
| --- | --- |
| Sodium Carboxymethylcellulose | 0.45% (wt/vol) |
| Sodium Saccharin | 0.075 g |
| Spearmint Oil | 0.375 ml |
| Methyl Paraben | 0.75 g |
| Propyl Paraben | 0.25 g |
| Water q.s. | 500 ml |

EXAMPLE 8

| Glycerin | 200 ml |
| --- | --- |

| | |
|---|---|
| Sodium Carboxymethylcellulose | 0.9% (wt/vol) |
| Sodium Saccharin | 0.15 g |
| Spearmint Oil | 0.75 ml |
| Methyl Paraben | 1.5 g |
| Propyl Paraben | 0.5 g |
| Water q.s. | 1000 ml |

Applicant's presently preferred formulation is listed in Example 7.

It will be understood by those skilled in the art who have the benefit of this disclosure that many variations of the above formulations are possible and that the spirit and scope of the present invention will be limited only by the following claims.

What is claimed is:

1. A method for reducing the discomfort associated with the wearing of mouth protectors during a period of physical activity comprising:

applying to a mouth protector a composition consisting essentially of a lubricating agent, a thickening agent, a pharmaceutically suitable sweetner, a pharmaceutically suitable flavoring agent, a preservative, and water; and thereafter inserting said mouth protector into the oral cavity.

2. The method of claim 1 wherein said composition additionally contains an emulsifier.

3. The method of claim 1 wherein said composition consists essentially of in relative proportion about 10 to about 200 ml of glycerine, about 0.45 to about 2.4% (wt/vol) of a thickening agent, about 0.075 to about 2 g pharmaceutically suitable sweetner, about 0.375 to about 1 ml pharmaceutically suitable flavoring agent, about 0.1 to about 1 gram of preservative, and about 100 to about 1,000 ml of water.

4. The method of claim 1 wherein said composition is sprayed onto said mouth protector.

5. The method of claim 1 where the lubricating agent is selected from the group consisting of glycerin, propylene glycol and polyethylene glycol.

6. The method of claim 1 where the thickening agent is selected from the group consisting of carboxyalkyl cellulose derivatives, natural gums, and colloidal clays.

7. The method of claim 1 where the preservative is selected from the group consisting of methyl paraben, propyl paraben, and a combination of methyl paraben and propyl paraben.

8. The method of claim 1 where the flavoring agent is selected from the group consisting of peppermint oil, citrus oil and spearmint oil.

9. The method of claim 1 where the sweetener is sodium saccharin.

10. The method of claim 3 where the thickening agent is selected from the group consisting of carboxyalkyl cellulose derivatives, natural gums, and colloidal clays.

11. The method of claim 3 where the sweetener is sodium saccharin.

12. The method of claim 3 where the flavoring agent is selected from the group consisting of peppermint oil and spearmint oil.

13. The method of claim 3 where the composition additionally contains about 2 ml of emulsifier.

14. The method of claim 3 where the preservative is selected from the group consisting of methyl paraben, propyl paraben or a combination of methyl paraben and propyl paraben.

* * * * *